United States Patent [19]

Perdijon

[11] 4,102,206

[45] Jul. 25, 1978

[54] DEVICE FOR INSPECTING A TUBE BY ULTRASONICS

[75] Inventor: Jean Perdijon, Saint Ismier, France

[73] Assignee: Commissariat a l'Energie Atomique, Paris, France

[21] Appl. No.: 813,098

[22] Filed: Jul. 5, 1977

[30] Foreign Application Priority Data

Jul. 21, 1976 [FR] France .................................. 76 22208

[51] Int. Cl.$^2$ ............................................. G01N 29/04
[52] U.S. Cl. ........................................ 73/644; 73/623; 73/642
[58] Field of Search .................. 73/623, 640, 642, 644

[56] References Cited

U.S. PATENT DOCUMENTS

| 3,028,752 | 4/1962  | Bacon    | 73/623 X |
| 3,121,324 | 2/1964  | Cowan    | 73/623 X |
| 3,916,675 | 11/1975 | Perdijon | 73/623 X |
| 4,008,603 | 2/1977  | Paulissen | 73/623 X |

FOREIGN PATENT DOCUMENTS

1,721,102  10/1965  U.S.S.R. .................................. 73/644

Primary Examiner—Richard C. Queisser
Assistant Examiner—John P. Beauchamp

Attorney, Agent, or Firm—Lane, Aitken, Dunner & Ziems

[57] ABSTRACT

Device for the inspection of tubes by ultrasonics comprising a probe constituted by an ultrasonic transducer fixed to a mirror which receives the ultrasonic wave emitted by the transducer and centered on the axis of the probe, means for moving the probe within the tube to be inspected and means for detecting the ultrasonic echos reflected by the tube, wherein it also comprises means for introducing an acoustic coupling liquid into the volume between the tube, transducer and mirror when the probe penetrates the tube to be inspected and for discharging said liquid when the probe leaves the tube, said means substantially comprising a flexible pocket reservoir filled with liquid and placed in the lower part of the probe and connected to the volume to be supplied with liquid, whereby said pocket is flattened when it penetrates the tube to be inspected following the probe, which has the effect of expelling part of the liquid contained therein in the direction of said volume, the said liquid returning by gravity into the pocket when the latter leaves the tube under inspection and reassumes its shape.

This device can be used for detecting transverse or longitudinal faults in tubes, as well as for measuring their diameter and thickness.

4 Claims, 2 Drawing Figures

DEVICE FOR INSPECTING A TUBE BY ULTRASONICS

BACKGROUND AND BRIEF SUMMARY OF THE INVENTION

The present invention relates to a device for inspecting a tube by ultrasonics.

The device according to the invention comprises a probe constituted by an ultrasonic transducer fixed to a mirror which receives the ultrasonic wave emitted by the transducer and centred on the axis of the probe, means for moving the probe within the tube to be inspected and means for detecting ultrasonic echos reflected by the tube.

The device according to the invention also comprises means for introducing an acoustic coupling liquid into the volume between the tube, transducer and mirror when the probe penetrates the tube to be inspected and for discharging said liquid when the probe leaves the tube, said means substantially comprising a flexible pocket reservoir filled with liquid and placed in the lower part of the probe and connected to the volume to be supplied with liquid, whereby said pocket is flattened when it penetrates the tube to be inspected following the probe, which has the effect of expelling part of the liquid contained therein in the direction of said volume, the said liquid returning by gravity into the pocket when the latter leaves the tube under inspection and reassumes its shape.

The device according to the invention can be adapted to the detection of transverse or longitudinal faults in tubes, as well as to the measurement of diameter and thickness of tubes. In the latter case it comprises a rotary perforated screen, positioned between the transducer and the tube to be inspected. The mirror which receives the ultrasonic wave emitted by the transducer can be:

conical, with an apex angle of 90° ± $i$, for detecting transverse faults with an incidence $i$;
conical, with an apex angle equal to 90°, for measuring the radial dimensions;
helical for detecting longitudinal faults.

BRIEF DESCRIPTION OF THE DRAWINGS

The characteristics and advantages of the present invention will become more apparent from the following description of a non-limitative embodiment with reference to the attached drawings, wherein show.

DETAILED DESCRIPTION OF THE PREFERRED EMBODIMENTS

Figure 1:
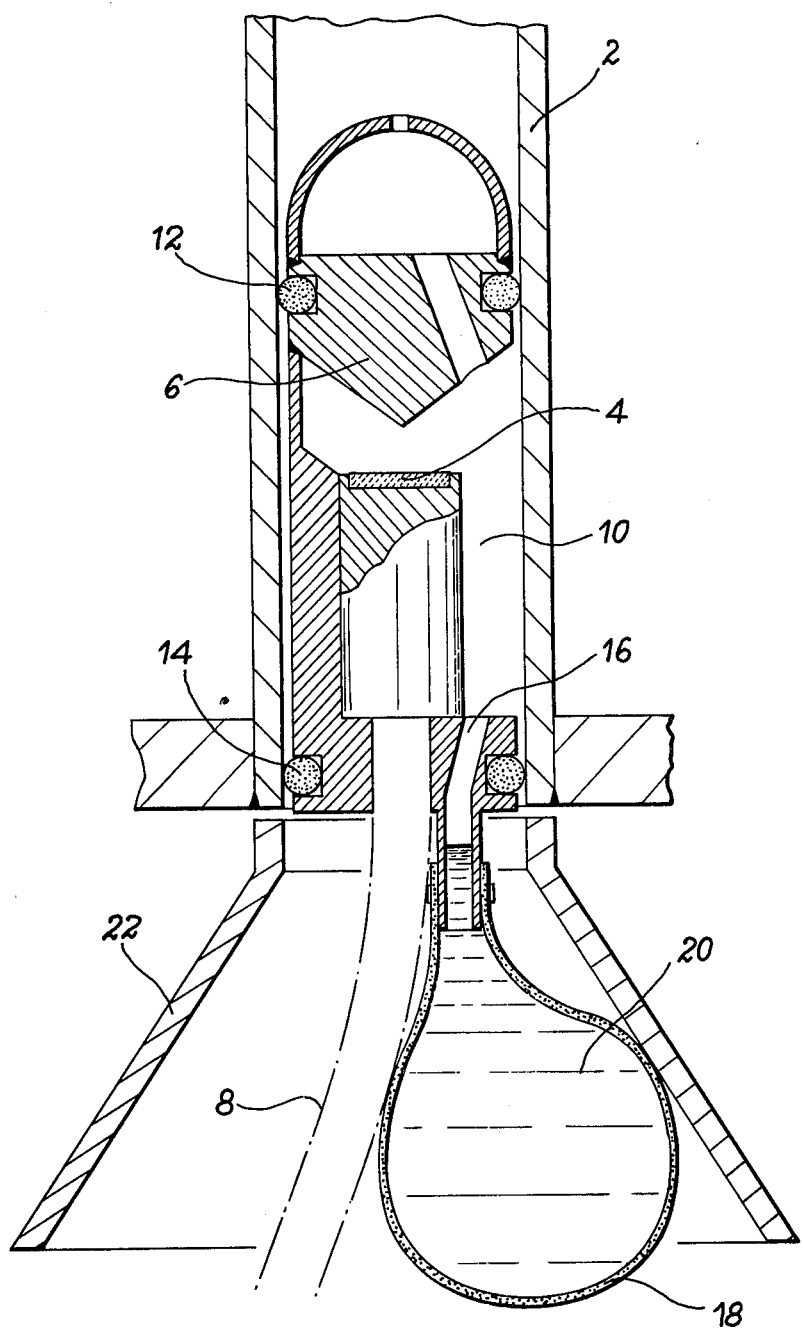
FIG. 1. The device according to the invention when the probe penetrates a tube to be inspected.

FIG. 1 shows in section a tube 2, whose quality or dimensions are to be inspected. Within the said tube moves a probe constituted by an ultrasonic transducer 4 fixed to a conical mirror 6 with an apex angle of 90° ± $i$, $i$ being the incidence angle. This probe is moved by means of a cable 8 controlled by a not shown pushing and pulling device. The volume 10 between tube 2, transducer 4 and conical mirror 6 is sealed by means of gaskets 12 and 14. Moreover, these gaskets centre the probe along the axis of the tube. This volume is linked by a pipe 16 with a pocket reservoir 18 filled with an acoustic coupling liquid 20. In the position illustrated in FIG. 1 the acoustic inspection probe occupies the lower position of tube 2 and pocket reservoir 18 is located in the widened portion 22 of a funnel which serves to guide the probe towards the tube to be inspected. The coupling liquid 20 is collected in the pocket reservoir and volume 10 is empty.

Figure 2:
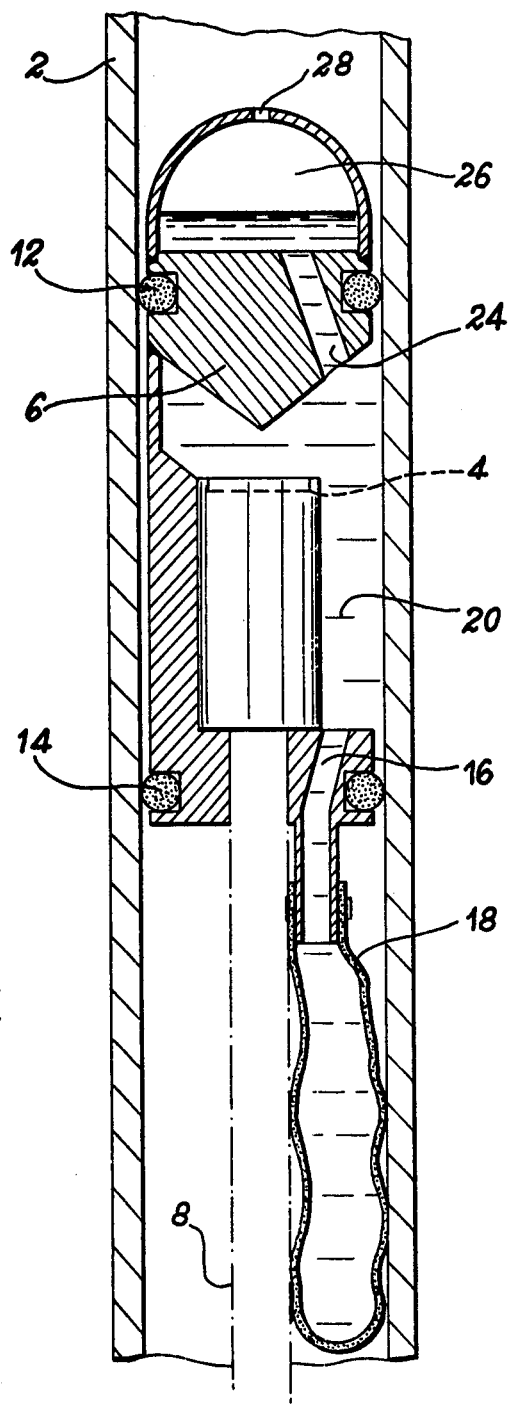
FIG. 2. The device when the probe is within the tube.

When the probe penetrates further forward into tube 2 the flexible pocket reservoir is flattened under the contraction action of the walls which guide it and liquid 20 is expelled towards the upper part. The arrangement obtained is shown in FIG. 2 where the components already described relative to FIG. 1 carry the same reference numerals. The liquid occupies volume 10, permitting acoustic coupling between transducer 4, conical mirror 6 and the walls of tube 2 to be inspected.

Conical mirror 6 is advantageously perforated by a pipe 24 connected to an overflow 26 which is connected to the atmosphere in the tube by an opening 28. Without passing beyond the scope of the invention the overflow 26 could advantageously be replaced by a flexible pocket reservoir.

The arrangement shown in FIG. 2 corresponds to the inspection phase of the tube. When the probe is removed after inspection the coupling liquid again collects in the pocket reservoir 18 as a result of gravity, when the latter has left the tube and reassumed its initial shape. Thus, once again the arangement of FIG. 1 is obtained.

A random coupling liquid can be used but preference is given to water.

In the embodiment shown in FIGS. 1 and 2 the probe is suitable for detecting transverse faults, but it is obvious that without passing beyond the scope of the invention the arrangement could be modified to make it suitable for the detection of longitudinal faults or for the measurement of the tube dimensions and in particular its internal and external diameters and its thickness. In the latter case the probe must have a rotary screen with at least one opening and arranged between the transducer and tube. In this embodiment the ultrasonic wave passes through the openings made in the screen and scans one area of the tube. The electronic means for detecting the echos and measuring the gaps between the echos, which are of conventional design and are consequently not described here, make it possible to determine the thickness and diameters of the tube.

Any flat piezoelectric transceiver transducer is suitable for the purposes of the present invention.

The means for moving the probe within the tube to be inspected are not described here because they are known. They can be identical to those generally used for moving an eddy current-operated probe within a tube. In general such an installation comprises a cable winding drum, a cable at the end of which is fixed the probe and a pushing and pulling device making it possible to move both cable and probe.

The invention can be applied to the inspection of any type of tube, but its preferred application is the in situ inspection of heat exchanger tubes for nuclear reactors. These tubes are generally made from an alloy of the Inconel type and have diameters of approximately 18 × 22 cm. They are positioned vertically and kept apart by spacers. The faults for which the inspection is being carried out consist for example of corrosion, cracks or thickness decreases. They are mainly located on the outer surface of the tube, which is not accessible during operation.

Hitherto such tubes could only be inspected in situ by the eddy current method, ultrasonic inspection only taking place after the manufacture of the tubes and prior to their being put into use. However, eddy current inspection is considerably disturbed by ferromagnetism of the tubes and by the existance of spacers. Thus, the device according to the present invention advantageously supplements the eddy current inspection method. The contamination risks which it causes are reduced because the acoustic coupling liquid is automatically collected in the pocket reservoir.

The invention is not limited to the embodiments described and represented hereinbefore and various modifications can be made thereto without passing beyond the scope of the invention.

What is claimed is:

1. A device for introducing an acoustic coupling liquid into a volume defined by an acoustic inspection probe and the walls of a tube to be inspected as the probe is inserted into said tube, comprising a flexible pocket reservoir filled with said liquid and associated with a lower portion of said probe, and a conduit between said pocket reservoir and the volume to be filled, whereby said pocket reservoir is compressed as the probe is inserted into said tube and at least part of the liquid in said reservoir is expelled via said conduit into the volume, said liquid returning to the pocket via said conduit under the force of gravity as the probe is removed from the tube permitting the flexible pocket to reassume its original shape.

2. A device according to claim 1, wherein the probe includes gaskets for sealing said volume and aligning said probe along the axis of the tube.

3. A device according to claim 1, wherein the probe includes a pipe between said volume and a second volume, said second volume serving to receive any overflow of the liquid from the volume being filled with said liquid.

4. A device according to claim 1, wherein the acoustic coupling liquid is water.

* * * * *